United States Patent [19]
Lashinski et al.

[11] Patent Number: 6,071,285
[45] Date of Patent: Jun. 6, 2000

[54] RAPID EXCHANGE FOLDED BALLOON CATHETER AND STENT DELIVERY SYSTEM

[76] Inventors: Robert D. Lashinski, 409 Princess Way; Dennis L. Brooks, 9261 Piccadilly Cir., both of Windsor, Calif. 95492; Philip J. Haarstad, 206 Kittery Point, Santa Rosa, Calif. 95403; Geoffrey A. Orth, 9145 St. James Pl, Windsor, Calif. 95492

[21] Appl. No.: 08/624,692

[22] Filed: Mar. 25, 1996

[51] Int. Cl.⁷ ...................................................... A61F 2/06
[52] U.S. Cl. .............................. 606/108; 623/1; 623/11; 604/96; 604/102; 606/191
[58] Field of Search .............................. 604/96, 102, 104, 604/264, 283; 606/108, 192, 194, 198, 191; 623/1, 11, 12

[56] References Cited

U.S. PATENT DOCUMENTS

| | | |
|---|---|---|
| 4,762,129 | 8/1988 | Bonzel . |
| 5,040,548 | 8/1991 | Yock . |
| 5,061,273 | 10/1991 | Yock . |
| 5,078,685 | 1/1992 | Colliver . |
| 5,267,958 | 12/1993 | Buchbinder et al. . |
| 5,330,499 | 7/1994 | Kanesaka . |
| 5,344,413 | 9/1994 | Allman et al. . |
| 5,383,853 | 1/1995 | Jung et al. . |
| 5,395,332 | 3/1995 | Ressemann et al. . |
| 5,409,458 | 4/1995 | Khairkhanhan et al. . |
| 5,413,557 | 5/1995 | Solar . |
| 5,443,457 | 8/1995 | Ginn et al. . |
| 5,458,639 | 10/1995 | Tsukashima et al. . |
| 5,484,449 | 1/1996 | Amundson et al. ..................... 606/198 |
| 5,496,346 | 3/1996 | Horzewski et al. . |
| 5,556,414 | 9/1996 | Turi ........................................ 606/198 |
| 5,575,771 | 11/1996 | Walinsky . |
| 5,613,981 | 3/1997 | Boyle et al. ............................ 606/198 |
| 5,669,932 | 9/1997 | Fischell et al. ......................... 606/198 |
| 5,674,241 | 10/1997 | Bley et al. .............................. 606/198 |
| 5,749,880 | 5/1998 | Banas et al. ............................ 606/198 |

OTHER PUBLICATIONS

Bjorn Nordenstrom, Balloon Catheters for Percutaneous Insertion Into The Vascular System, Mar. 2, 1962.

*Primary Examiner*—Glenn K. Dawson
*Attorney, Agent, or Firm*—Richard L. Klein

[57] ABSTRACT

The balloon portion of a balloon catheter for implanting a stent structure is at least initially retained laterally to a guide wire by passing the guide wire axially along the balloon inside the stent structure but not through the interior of the balloon or any permanent guide wire lumen at the location of the balloon. The initially deflated balloon may be folded laterally into a plurality of folds, and the guide wire may pass between the folds or outside the folds as desired. Guide wire lumens may be provided distally and/or proximally of the balloon. An elastic sleeve may be provided around the balloon to help keep the balloon folded prior to inflation and to help refold the balloon during and after deflation. If an elastic sleeve is provided, the guide wire may pass along the balloon inside the sleeve.

78 Claims, 7 Drawing Sheets

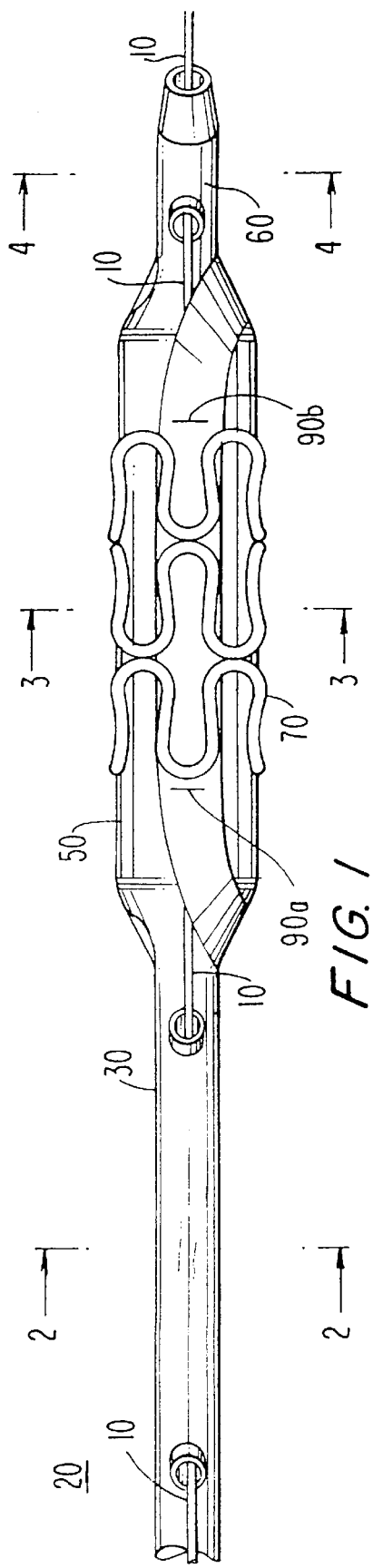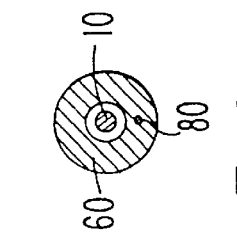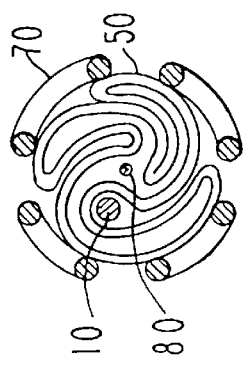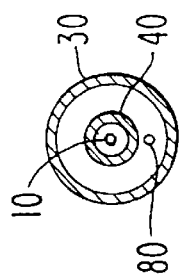

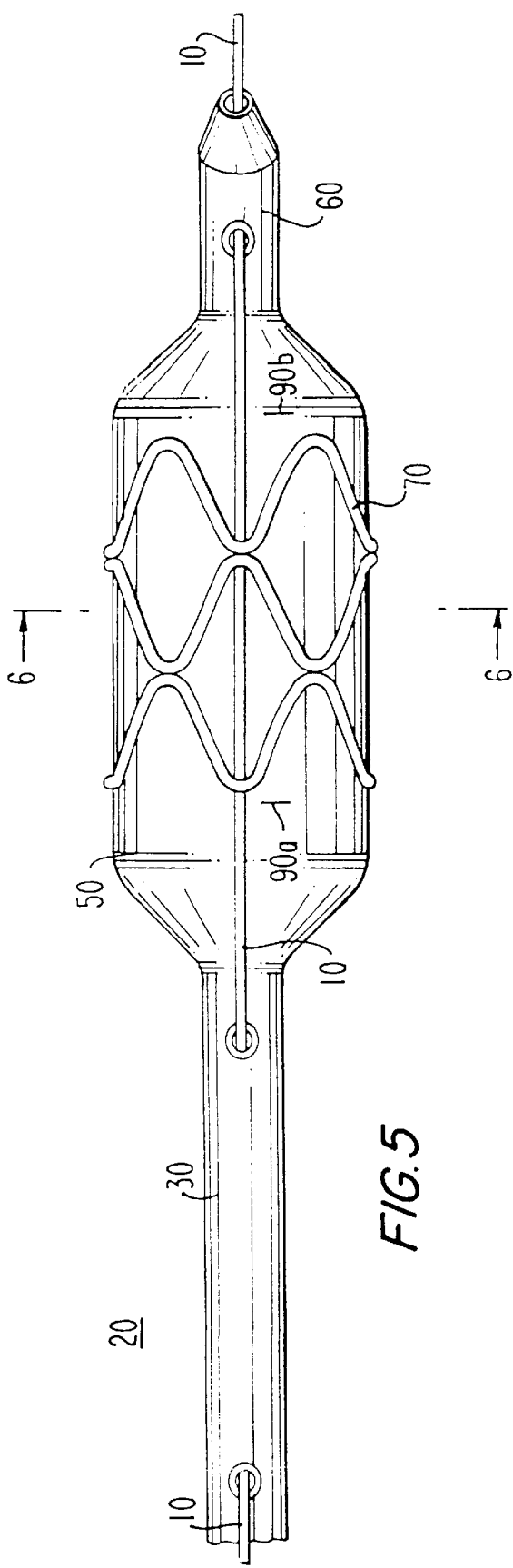
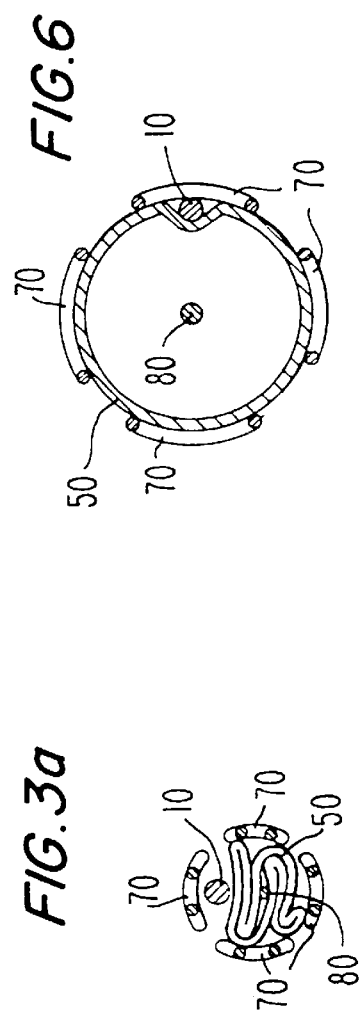

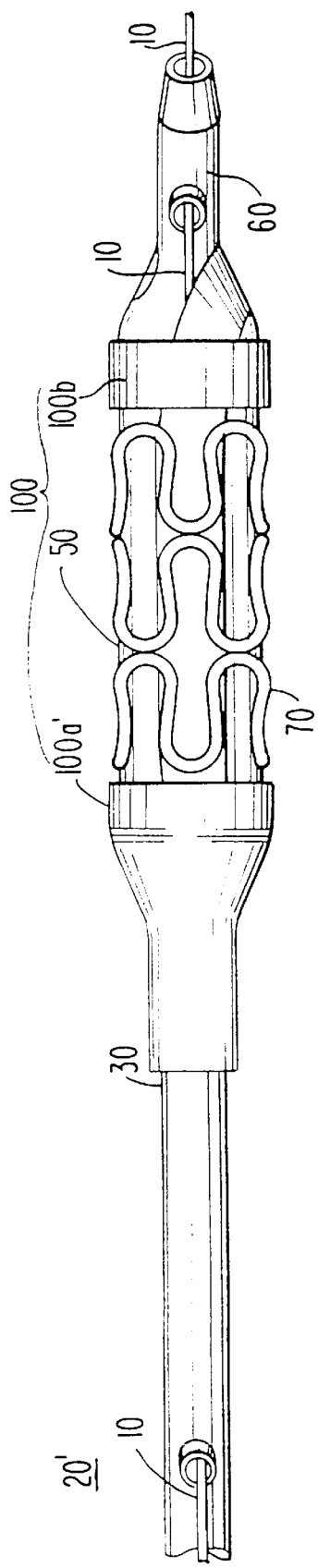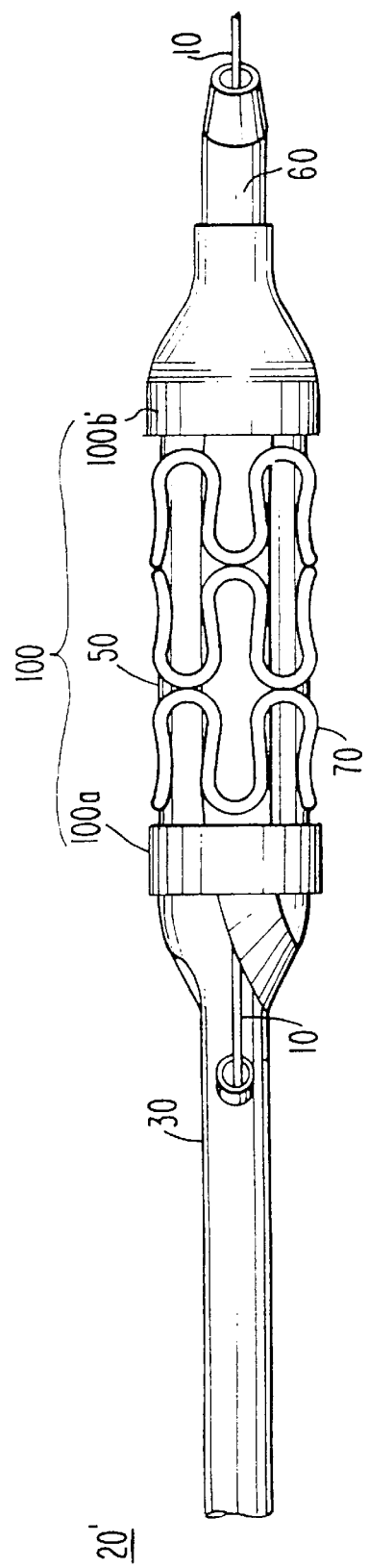

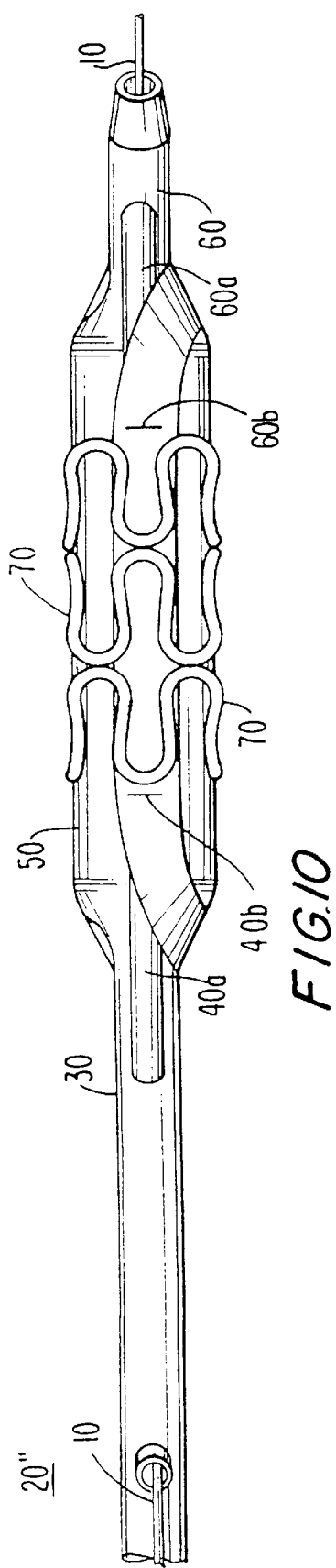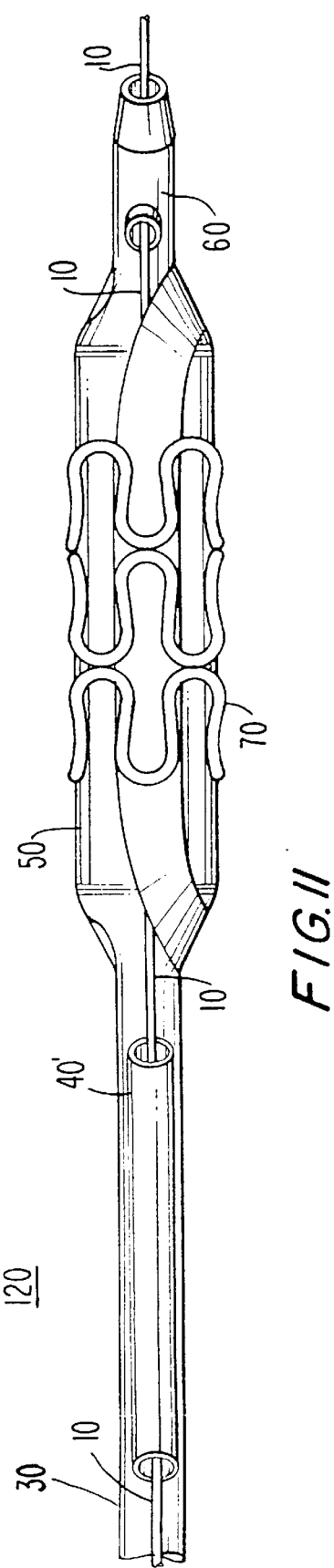

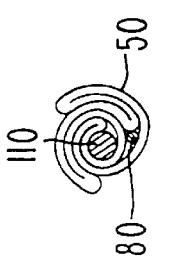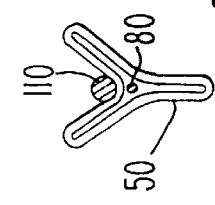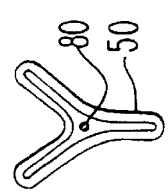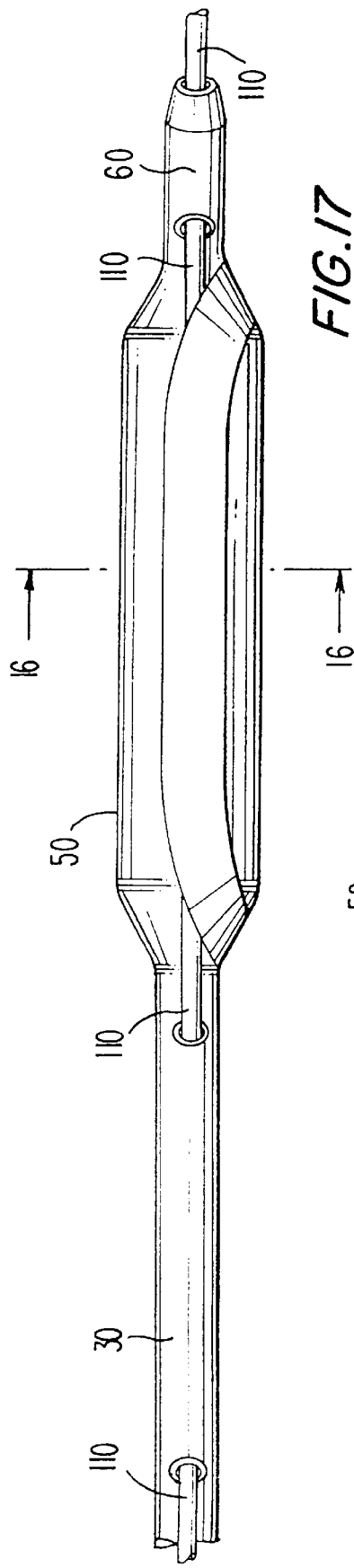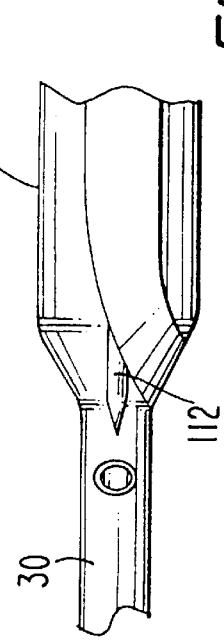

RAPID EXCHANGE FOLDED BALLOON CATHETER AND STENT DELIVERY SYSTEM

BACKGROUND OF THE INVENTION

This invention relates to dilatation catheters and stents for dilating structures or stenoses in the human body. More particularly, the invention relates to balloon catheter and stent delivery systems which have increased flexibility and kink resistance, and which may also have a reduced cross section at the balloon and stent prior to inflation of the balloon.

The use of balloon catheters to treat structures, stenoses, or narrowings in various parts of the human body is well known in the prior art. Examples of such catheters are shown in Bonzel U.S. Pat. No. 4,762,129, Yock U.S. Pat. No. 5,040,548, Kanesaka U.S. Pat. No. 5,330,499, Solar U.S. Pat. No. 5,413,557, and Tsukashima et al. U.S. Pat. No. 5,458,639.

An illustrative procedure involving balloon catheters is known as percutaneous translumenal coronary angioplasty, which may be used to reduce arterial build-up of cholesterol fats or atherosclerotic plaque. This procedure involves passing a balloon catheter over a guide wire to a stenosis. Once positioned appropriately (e.g., under fluoroscopic guidance), the balloon is inflated, which breaks the plaque of the stenosis and causes the arterial cross section to increase. Then the balloon is deflated and withdrawn over the guide wire.

In many cases, a stent must be implanted to provide permanent support for the artery. When a stent is to be implanted, the usual practice is to first dilate the stenosis with a first balloon catheter that does not carry a stent. Then the first catheter is withdrawn over the guide wire and a second catheter which does carry a stent on its balloon is inserted via the guide wire. When the balloon of the second catheter is at the location of the stenosis, that balloon is inflated to circumferentially expand and thereby implant the stent. Thereafter, the balloon of the second catheter is deflated and the second catheter and the guide wire are withdrawn from the patient.

Rapid exchange balloon catheters are those that facilitate rapid removal and replacement of catheters on a guide wire. After a first catheter has been placed in the patient on the guide wire, the physician may wish to remove that catheter and replace it with another catheter having a larger dilatation balloon or an implantable stent as described above. The guide wire is left substantially in place during these catheter removal and replacement steps. To facilitate rapid removal and replacement of catheters, catheters have been designed with relatively short guide wire lumens (e.g., Kanesaka U.S. Pat. No. 5,330,499 and Solar U.S. Pat. No. 5,413,557), which decrease frictional resistance and eliminate the need for extension guide wires that may be necessary when longer guide wire lumens are used. For example, by providing only a relatively short guide wire lumen at or in the vicinity of the balloon, the length of the guide wire outside the patient can be made considerably shorter than if the guide wire lumen extends along the entire length of the catheter. (Some length of guide wire must be outside the patient and outside the catheter guide wire lumen at substantially all times so that a grip can be maintained on the guide wire.) In particular, the length of the guide wire outside the patient can be made only slightly longer than the length of the relatively short guide wire lumen. This makes it possible to shorten the stroke of a catheter being withdrawn (because it is only necessary to withdraw the distal end of the guide wire lumen past the proximal end of the shorter guide wire). Similarly, the stroke of the replacement catheter can be greatly shortened (because it is only necessary to begin feeding the distal end of the replacement catheter's guide wire lumen onto the proximal end of the shorter guide wire). Shortening the two catheter strokes in this way greatly speeds up the catheter removal and replacement operation, leading to the characterization of this type of catheter as a "rapid exchange" catheter.

The rapid exchange balloon catheters in the prior art include multi-lumen (Solar U.S. Pat. No. 5,413,557) or coaxial lumen (Kanesaka U.S. Pat. No. 5,330,499) designs at the balloon site. The result of these designs is a relatively large cross-section balloon region due to the extra lumen through which the guide wire passes. Because of the larger cross section, the balloon catheter may encounter greater resistance while negotiating a tortuous body passageway or vessel. In addition, the balloon may resist entering a stenosis, possibly bunching or folding when attempting to make such entry. If a stent is mounted on the balloon, the stent may cause the cross section to be even larger, thereby exacerbating these problems.

One way to decrease the balloon catheter cross section is to eliminate the extra guide wire lumen at the balloon site. A 1962 article by Nordenstrom may suggest this possibility. Nordenstrom shows a catheter with a guide wire exiting a guide wire lumen distal of the balloon. In Nordenstrom's disclosure, however, the guide wire is not restricted adjacent the balloon. This may be undesirable, and so subsequent catheter designs (e.g., the above-mentioned Solar and Kanesaka designs) contained the movement of the guide wire by extending the guide wire lumen to a point proximal of the balloon.

In view of the foregoing, it is an object of this invention to provide improved catheters and methods for use with guide wires and stents.

It is a more particular object of this invention is to provide balloon catheters having a smaller cross section at the balloon than those in the prior art, and which are more easily and rapidly placed on or removed from guide wires.

SUMMARY OF THE INVENTION

These and other objects of the invention are accomplished in accordance with the principles of the invention by providing catheters in which the balloon is initially folded within an annular stent structure and the guide wire passes through this assembly without the need to pass through the inflatable interior of the balloon or any actual lumen at the location of the balloon in order for the guide wire to be retained adjacent the balloon. The annular stent structure may directly retain the balloon and guide wire together, and the stent may additionally help to keep the balloon initially folded. Alternatively, the balloon may be folded so that the guide wire can pass between folds of the balloon, and the stent may help maintain this folded condition of the balloon. Because there is no need for any actual guide wire lumen at the axial location of the balloon, the cross section of the assembly may be reduced. A smaller cross section helps the catheter pass along a tubular body structure more easily. It also helps make the balloon more flexible so that it can more easily negotiate tortuous portions of the tubular body structure. Elimination of the guide wire lumen at the location of the balloon also helps make the balloon more flexible.

If desired, a guide wire lumen may be provided distal and/or proximal of the balloon. The tubing of the distal and/or proximal guide wire lumens may extend a short way into the balloon folds (exterior of the inflatable interior of the balloon) to help guide an end of the guide wire axially into and then out of the folded balloon structure. However, these guide wire lumen extensions preferably end short of the axial ends of the stent so that they do not increase the cross section of the structure at the stent.

The catheter is typically provided with a pusher or support wire, which extends from a proximal portion of the catheter to a point distal of the balloon. The distal end of the pusher wire is preferably securely attached to the catheter. A preferred material for the pusher wire is nitinol (nickel-titanium) because of its very high flexibility and elasticity, which will help prevent kinking of any portion of the catheter through which it passes. Radio-opaque markers may be provided on the pusher wire at predetermined locations near the stent (e.g., adjacent each axial end of the stent) to facilitate positioning the stent at the desired location in the body.

The balloon may be constructed and/or treated so that it tends to refold with a relatively compact cross section after it has been inflated and deflated. This feature facilitates withdrawal of the deflated catheter from the patient.

In addition to the stent, an annular elastic sleeve structure may be placed around the balloon. The guide wire may pass either inside or outside the elastic sleeve structure, as desired. If provided, the elastic sleeve structure may help keep the balloon initially folded, and it may also help the balloon refold compactly after the balloon has been deflated. If the guide wire passes inside the elastic sleeve structure (and assuming that the elastic sleeve extends along the length of the stent inside the stent), the sleeve may help keep the guide wire from contacting the stent, but such contact is not a concern for most embodiments of the invention. A preferred embodiment of the elastic sleeve structure does not axially overlap the stent structure, but rather has sleeve portions that are axially beyond the axial ends of the stent. The elastic sleeve structure may extend axially from the balloon beyond the point at which the guide wire exits from a proximal and/or distal guide wire lumen in order to pass along the balloon. If provided, such an extension of the elastic sleeve structure helps guide the guide wire between the proximal or distal lumen and the balloon.

A preferred method of making catheters in accordance with this invention includes deflecting the balloon into a plurality of radially and axially extending "wings" spaced from one another in the circumferential direction around the central longitudinal axis of the balloon. The balloon is initially basically cylindrical, and the abovementioned wings may be formed by radially inwardly deflecting circumferentially spaced axial portions of the balloon surface. This may be done, for example, by passing the balloon axially through a guide. A rodlike mandrel having a diameter which is somewhat larger than the diameter of the guide wire with which the catheter is to be used is placed axially along the balloon between two of the above-mentioned wings. This may be done, for example, by passing the mandrel through the above-mentioned guide with the balloon. The mandrel also preferably extends into the guide wire lumens that are distal and proximal of the balloon. The balloon wings are then wrapped or folded laterally around the mandrel in the manner in which it is desired that the balloon will be folded around or adjacent to the guide wire when the catheter is used. A temporary sleeve may be placed around the folded balloon and mandrel, and this structure is heated (e.g., by heating the mandrel) to give the balloon a heat set "memory" of its folded condition. This heating may also create "ramps" or valleys (or may help to reinforce previously formed ramps or valleys) in the catheter tubing and tapered ends of the balloon where the catheter tubing and balloon join. These valley-like ramps or slight radially inward depressions caused (or reinforced) by contact with the above-described mandrel during heating help to give the balloon a preferred folding plane which promotes the desired refolding of the balloon when it is deflated toward the end of its use in a patient. The mandrel is withdrawn axially after the above-described heating. The withdrawn mandrel leaves behind a clearance through which a guide wire can be passed. The stent (and the above-described elastic sleeve structure, if provided) may be placed around the balloon at any convenient time after folding of the balloon.

In a typical use of catheters constructed in accordance with this invention, the catheter is fed into a tubular body structure along a guide wire that is already in place in that body structure. (For example, the guide wire may have been employed with another balloon catheter that was used to preliminarily dilate the body structure that is to receive a stent.) At the location of the balloon, the guide wire passes inside the annular stent, and it may also pass between folds of the balloon. If an elastic sleeve is provided around the balloon inside the stent structure, the guide wire may pass either inside or outside that sleeve. Similarly, if shorter elastic sleeves are provided only beyond the axial ends of the stent, the guide wire may pass either inside or outside of those sleeves. When the balloon and stent are at the desired location in the body structure, the balloon is inflated. This circumferentially expands and implants the stent. Any elastic sleeve structure around the balloon is also circumferentially expanded. After the stent has been implanted, the balloon is deflated and the catheter (including any elastic sleeve structure) is withdrawn from the patient along the guide wire. Assuming that there is no further need for the guide wire, the guide wire may also be withdrawn.

Further features of the invention, its nature and various advantages, will be more apparent from the accompanying drawings and the following detailed description of the preferred embodiments.

BRIEF DESCRIPTION OF THE DRAWINGS

FIG. 1 is a simplified, partial, elevational view of an illustrative embodiment of a balloon catheter constructed in accordance with this invention prior to inflation of the balloon.

FIG. 2 is a simplified sectional view taken along the line 2—2 in FIG. 1.

FIG. 3 is a simplified sectional view taken along the line 3—3 in FIG. 1.

FIG. 3a is a view similar to FIG. 3 illustrating an alternative embodiment of the invention.

FIG. 4 is a simplified sectional view taken along the line 4—4 in FIG. 1.

FIG. 5 is a simplified, partial, elevational view of the catheter of FIG. 1 after inflation of the balloon.

FIG. 6 is a simplified sectional view taken along the line 6—6 in FIG. 5.

FIG. 7a is a view similar to FIG. 7 showing a possible modification of the FIG. 7 embodiment in accordance with this invention.

FIG. 7b is another view similar to FIG. 7 showing another possible modification of the FIG. 7 embodiment in accordance with this invention.

FIG. 10 is another view similar to FIG. 1 showing still another illustrative embodiment of the invention.

FIG. 11 is still another view similar to FIG. 1 showing yet another illustrative embodiment of the invention.

FIG. 14 is a simplified cross sectional view of an illustrative catheter during processing in accordance with this invention.

FIG. 15 is similar to FIG. 14, additionally showing certain illustrative catheter processing tooling in accordance with this invention.

FIG. 16 is again similar to FIGS. 14 and 15, but shows a later stage of processing in accordance with this invention. FIG. 16 is taken along the line 16—16 in FIG. 17.

FIG. 17 is a simplified, partial, elevational view of a catheter and catheter processing tooling during processing in accordance with this invention.

FIG. 18 is similar to a portion of FIG. 17 after removal of the catheter processing tooling.

DETAILED DESCRIPTION OF THE PREFERRED EMBODIMENTS

Figure 7:
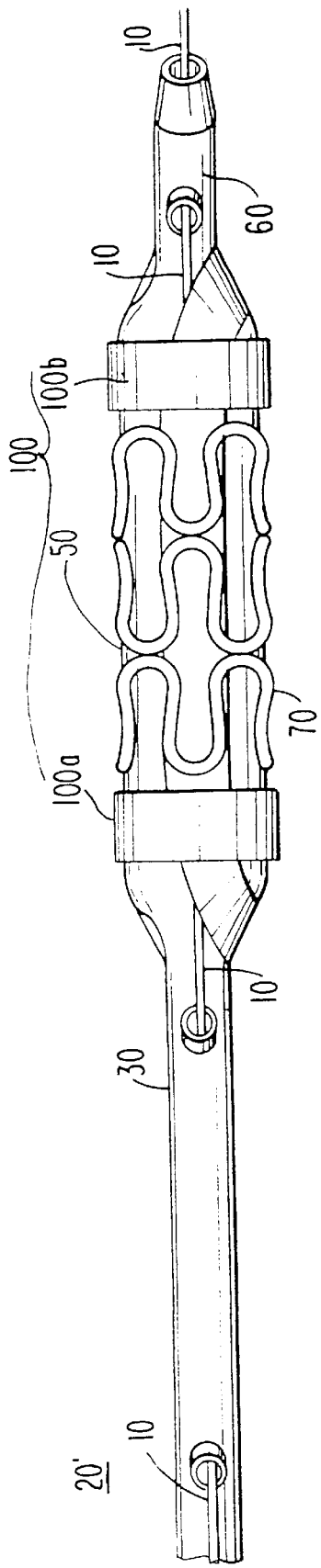
FIG. 7 is a view similar to FIG. 1 showing another illustrative embodiment of the invention.

An illustrative embodiment of a catheter 20 constructed in accordance with this invention is shown in FIG. 1. The proximal portion of catheter 20 is toward the left in FIG. 1, and the distal portion is toward the right. Catheter 20 is shown on a guide wire 10, although it will be understood that the guide wire is a separate component which is not really part of the catheter.

Catheter 20 includes an inflation lumen 30, a proximal guide wire lumen 40 (inside a distal portion of inflation lumen 30), a balloon portion 50, and a distal guide wire lumen 60. Inflation lumen 30 extends from a portion of the catheter which always remains outside the patient and which is not shown in FIG. 1 because it can be conventional. Inflation lumen 30 is in fluid communication with the interior of balloon 50. Thus inflation lumen 30 is used to supply pressurized inflation fluid to balloon 50 when it is desired to inflate the balloon. Inflation lumen 30 is also used to drain inflation fluid from balloon 50 when it is desired to deflate the balloon. Proximal guide wire lumen 40 opens out through the wall of inflation lumen 30 at two axially spaced points along the distal portion of the inflation lumen. Guide wire 10 passes through lumen 40 (see also FIG. 2). Lumen 40 can be of any desired length along lumen 30, but it is preferably relatively short and relatively close to balloon 50 because this gives catheter 20 more of a rapid exchange construction.

Balloon 50 is initially deflated and folded laterally in on itself as shown in FIG. 1 (see also FIG. 3). Guide wire 10 may pass along balloon 50 through a clearance between folds in the balloon as shown in FIG. 3, or the guide wire may pass along balloon 50 through a clearance outside the folds but inside stent structure 70 as shown in FIG. 3a. In either case it is important to note that the guide wire does not pass through the inflatable interior of balloon 50. This is what is meant when it is said that guide wire 10 passes outside the balloon. It is also important to note that no lumen structure is needed or provided for the guide wire at the axial location of the balloon.

An annular metal stent structure 70 is disposed around balloon 50 (and guide wire 10 where it passes outside balloon 50). Stent structure 70 is initially circumferentially compressed around balloon 50 and helps to keep the balloon folded with a relatively compact cross section. However, this structure is preferably not so circumferentially compressed that it is difficult to pass guide wire 10 through the structure or to slide the structure along the guide wire. Although stent structure 70 may be constructed in many different ways, an example of a suitable stent construction is shown in Boneau U.S. Pat. No. 5,292,331, which is hereby incorporated by reference herein.

Distal of balloon 50, catheter 20 continues—typically for only a relatively short distance—with a distal guide wire lumen 60. Although attached to balloon 50, lumen 60 is not in fluid communication with the interior of the balloon. Guide wire 10 passes through lumen 60 (see also FIG. 4), and may extend from the open distal end of that lumen.

Although it is not visible in FIG. 1, FIGS. 2–4 show that a pusher wire 80 extends along most of the length of catheter 20, from a proximal end (which may be attached to stainless steel hypotube having an axial portion which remains outside the body of the patient at all times), through the interior of inflation lumen 30, through the interior of balloon 50, and into the material of distal guide wire lumen 60. (See also FIGS. 12 and 13, which show additional details regarding illustrative constructions of pusher wire 80 and related components.) The distal end of pusher wire 80 is firmly anchored in lumen 60. Pusher wire 80 facilitates pushing catheter 20 in the distal direction along guide wire 10 without allowing any portion of the catheter (and especially balloon 50) to kink, prolapse, or otherwise undesirably deform. In the unlikely event that a distal portion of the catheter becomes separated from the proximal portion (e.g., as a result of the balloon tearing), the secure anchoring of the distal end of pusher wire 80 in distal guide wire lumen 60 makes it possible to use the pusher wire to pull the separated distal portion out of the patient. A particularly preferred material for pusher wire 80 is nitinol (nickel-titanium). This material is particularly advantageous because it is extremely flexible and elastic. It is therefore very effective in allowing the catheter to flex without kinking.

Radio-opaque markers are preferably provided on pusher wire 80 adjacent to each axial end of stent 70. In FIG. 1, for example, preferred axial locations for such radio-opaque markers are indicated by the lines 90a and 90b, and the radio-opaque markers will therefore be referred to by reference designations 90a and 90b. (See also FIGS. 12 and 13 where illustrative radio-opaque markers 90a and 90b are actually shown.) When the catheter is in use, markers 90a and 90b facilitate axially positioning the catheter so that stent 70 is at the desired location along the tubular body structure in which it is being used.

In use, catheter 20 is fed into a patient along guide wire 10, which is already in place in the patient. For example, guide wire 10 may have already been used with another balloon catheter for the purpose of preliminarily dilating a body structure that is to receive the stent 70 from catheter 20. Guide wire 10 will then have been left in the patient when the other catheter is withdrawn from the patient along the wire. Catheter 20 may be placed on guide wire 10 by threading distal guide wire lumen 60, then balloon 50, and finally proximal guide wire lumen 40 on the proximal end of guide wire 10, which remains outside the patient at all times. Then the catheter is fed into the patient along the guide wire. Pusher wire 80 may be used to push the catheter in the distal direction along the guide wire. An initial portion of the entry of the guide wire and catheter into the patient may be made via a conventional guide catheter.

When balloon 50 is at the location in the patient's tubular body structure that is to receive stent 70 (which may be determined with the aid of radio-opaque markers 90), pressurized balloon inflation fluid is supplied to balloon 50 via inflation lumen 30. This causes balloon 50 to unfold and inflate as shown in FIGS. 5 and 6. Inflation of balloon 50 circumferentially expands stent structure 70 as is also shown in FIGS. 5 and 6. Note that guide wire 10 remains outside inflated balloon 50 but inside circumferentially expanded stent structure 70. Circumferential expansion of stent structure 70 permanently implants the stent structure in the patient's tubular body structure.

After balloon 50 has been inflated and stent structure 70 thereby implanted as described above, balloon 50 is deflated by draining the inflation fluid from it via lumen 30. This allows the balloon to collapse and preferably refold. (Illustrative methods for making catheter 20 to promote efficient refolding of the balloon are discussed later in this specification.) Catheter 20 can then be withdrawn from the patient by pulling it out along guide wire 10. If there is no further need for guide wire 10, the guide wire can also be withdrawn from the patient.

Figure 9:
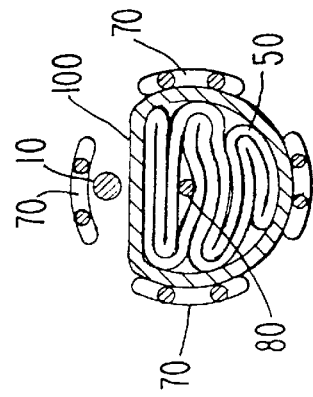
FIG. 9 is another view similar to FIG. 3 showing yet another illustrative embodiment of the invention.
Figure 8:
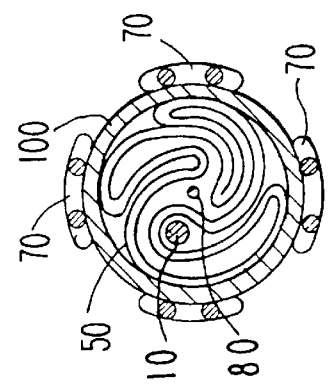
FIG. 8 is a view similar to FIG. 3 showing still another illustrative embodiment of the invention.

Another feature that catheters constructed in accordance with this invention may have is illustrated by the alternative embodiment 20' shown in FIG. 7. This feature is an annular elastic sleeve structure 100 around at least a portion of the axial length of balloon 50. In the particular embodiment shown in FIG. 7, elastic sleeve structure 100 includes two portions 100a and 100b around balloon 50 beyond the respective axial ends of stent structure 70. In the alternative embodiments shown in FIGS. 8 and 9 stent structure 70 at least partly axially overlaps sleeve structure 100 so that the sleeve structure is inside the stent. In the FIG. 8 embodiment, guide wire 10 passes inside of elastic sleeve 100. In the FIG. 9 alternative, guide wire 10 passes between elastic sleeve 100 and stent 70. In all cases (i.e., any of FIGS. 7–9) the elastic sleeve structure 100 helps to keep balloon 50 folded prior to inflation. During inflation the elastic sleeve structure expands circumferentially with the balloon and stent. During deflation the elastic sleeve helps to compactly refold the balloon. The embodiment shown in FIG. 7 has the advantage that elastic sleeve structure 100 does not increase the diameter of the catheter at the balloon by being inside the stent. The embodiments shown in FIGS. 7 and 8 have the advantage that the elastic sleeve structures 100 help to prevent guide wire 10 from contacting stent 70. However, contact between the guide wire and the stent may not be a significant concern, and so the embodiment shown in FIG. 9 may also be useful. Elastic sleeve structure 100 may be made of any suitable material such as silicone rubber, latex rubber, or elastomeric polyurethane.

FIG. 7a shows a possible modification of what is shown in FIG. 7 in accordance with the invention. In FIG. 7a proximal elastic sleeve 100a' extends in the proximal direction past the distal end of proximal guide wire lumen 40 (which lumen may be as shown, for example, in FIGS. 1, 2, and 7). In this way sleeve 100a' aids in inserting or loading the proximal end of guide wire 10 into proximal guide wire lumen 40 as the catheter is being fed onto the guide wire. The modification shown in FIG. 7a may also be used with embodiments of the type shown in FIG. 8.

FIG. 7b shows that the principle illustrated by 7a is equally applicable to the distal end of the balloon. In FIG. 7b distal elastic sleeve 100b' extends in the distal direction past the proximal opening of distal guide wire lumen 60 (which lumen may be as shown, for example, in FIGS. 1, 4, and 7). In this way sleeve 100b' aids in inserting or loading the proximal end of guide wire 10 into the guide wire clearance associated with balloon 50 as the catheter is being fed onto the guide wire. The modification shown in FIG. 7b may be used with the modification shown in FIG. 7a, and it may also be used with embodiments of the type shown in FIG. 8.

Still another feature that the catheters of this invention may have is shown in FIG. 10. This feature is extension 40a of the proximal guide wire lumen 40 into the folds of balloon 50, and/or the similar extension 60a of the distal guide wire lumen into the folds of the balloon. Extensions 40a and 60a preferably end before reaching the interior of stent 70 so that they do not combine with the stent to increase the diameter of the catheter 20" in its balloon region. Thus the line 40b indicates the approximate preferred location of the distal end of extension 40a, and line 60b indicates the approximate preferred location of the proximal end of extension 60a. If provided, extensions 40a and 60a help guide the proximal end of the guide wire into the distal end of the folded balloon and then into the distal end of lumen 40 inside inflation lumen 30.

Another illustrative variation 120 of the invention is shown in FIG. 11. In catheter 120 proximal guide wire lumen 40' runs along the outside of inflation lumen 30. Lumen 40' may be formed unitarily with lumen 30, or it may be secured to lumen 30 in any other suitable way (e.g., by adhesive or by a shrink tube around both lumens).

Figure 12:
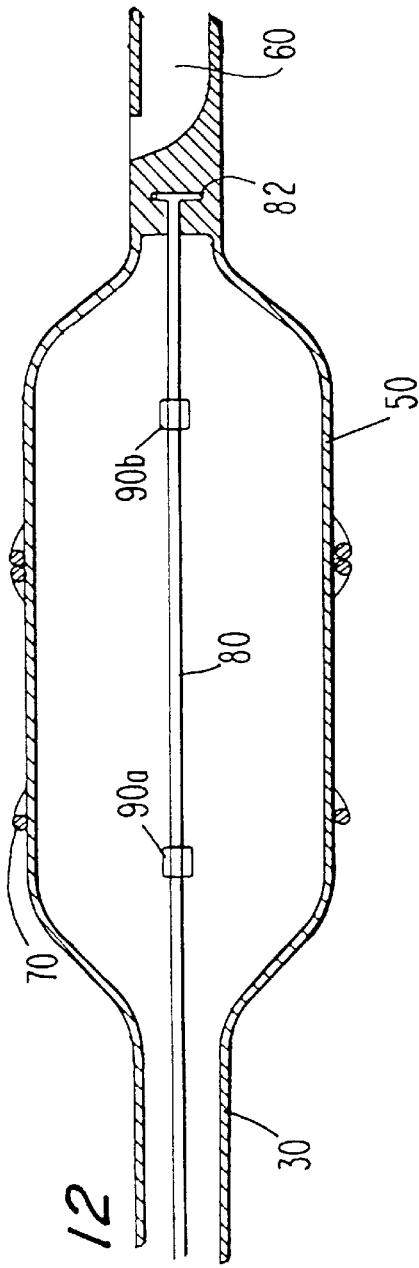
FIG. 12 is a simplified longitudinal sectional view of a portion of an illustrative catheter constructed in accordance with this invention.

FIG. 12 shows an illustrative way in which the distal end of pusher wire 80 may be secured in the material of the catheter distal of balloon 50. In this embodiment pusher wire 80 has a radially enlarged distal end 82 which is molded or otherwise embedded in the catheter between the distal end of balloon 50 and the proximal beginning of guide wire lumen 60. FIG. 12 also shows illustrative radio-opaque markers 90a and 90b on pusher wire 80.

Figure 13:
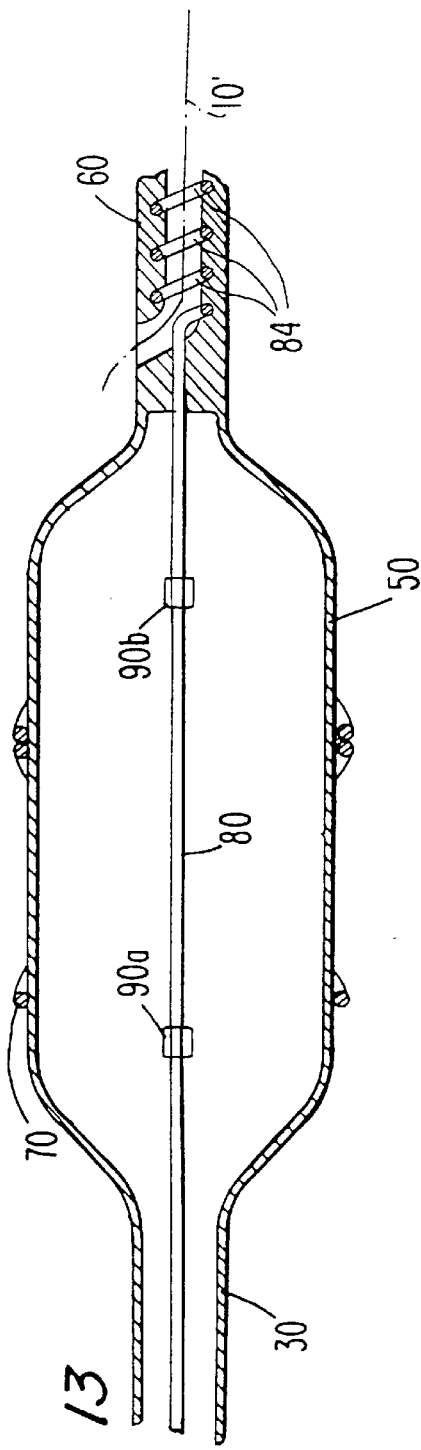
FIG. 13 is another view similar to FIG. 12 showing another illustrative catheter construction in accordance with this invention.

FIG. 13 shows an alternative way of securing the distal end of pusher wire 80 to the catheter distal of balloon 50. In this embodiment the distal end of pusher wire 80 is formed into a coil 84. The material of distal guide wire lumen 60 is then at least partly molded around coil 84 so that the coil becomes an integral part of the distal guide wire lumen. The guide wire (not shown in FIG. 13) passes through the center of coil 84 and out the opening in the side of lumen 60 as indicated by the chain-dotted line 10'.

As has been mentioned, secure attachment of the distal end of pusher wire 80 to the portion of the catheter distal of balloon 50 (e.g., as shown in FIG. 12 or FIG. 13) ensures that if the balloon tears during use, pusher wire 80 can be used to pull the portion of the catheter which is distal of the tear out of the patient.

Other than the differences discussed above, the construction and operation of catheters 20', 20", and 120 may be the same as the construction and operation of catheter 20. The various components of the catheters of this invention can be made of the same materials that are conventionally used for generally corresponding components of known catheters. Thus, for example, the various lumens can be made of materials such as polyethylene, polyethylene terephthalate, polyurethanes, polyesters, and copolymers thereof. As another example, at least part of inflation lumen 30 may be stainless steel hypotube or the like. The material of balloon 50 may be polyethylene, polyethylene terephthatate, nylon, polyamides, latex rubber, or the like. Stent structure 70 can be of any conventional construction (e.g., wire, tubular, or braided) and can be made of any conventional stent material (e.g., stainless steel, tantalum, titanium, or nitinol). Guide wire 10 and pusher wire 80 can also be of any conventional construction and material. For example, solid or braided stainless steel wire or stainless steel hypotube may be used. Thus it will be seen that the term "wire" is used for these elements only as a matter of convenience, and that they may not actually be wire. As has been mentioned, an especially preferred material for pusher wire 80 is nitinol wire. Suitable materials for elastic sleeve structure 100 are mentioned above. The dimensions (e.g., the lengths, diameters, thicknesses, etc.) of various components of the catheters of this invention may be similar to the dimensions that are conventionally used for generally corresponding components of known catheters.

Illustrative methods for making catheters in accordance with this invention are illustrated by FIGS. 14–17. After balloon 50 has been formed, it is shaped so that it has several radially and axially extending wings spaced from one another circumferentially around a central longitudinal axis of the balloon (see FIG. 14). Balloon 50 may be shaped in this way, for example, by passing it axially through an appropriately shaped guide. Pusher wire 80 is preferably placed in balloon 50 before the balloon is shaped as shown in FIG. 14.

An elongated rod-like mandrel 110 is placed between two of the wings of balloon 50 as shown in FIG. 15. This may be done by passing the mandrel through the above-mentioned guide with the balloon. Indeed, the mandrel may help the balloon pass through the guide. The mandrel preferably also extends into guide wire lumens 40 and 60 (see FIG. 17). The diameter of mandrel 110 is preferably somewhat larger than the guide wire 10 with which the catheter will be used.

A further step is to fold the wings of balloon 50 laterally in a predetermined direction around mandrel 110 as shown, for example, in FIGS. 16 and 17. A sleeve (which may be temporary and which is not shown in the drawings) may be placed around the folded balloon to help keep it folded.

A still further step is to heat the catheter so that it takes a heat set which tends to keep balloon 50 in the folded condition. The catheter may be heated, for example, by heating mandrel 110. The heat set thus given to balloon 50 will also help it to refold when it is deflated during use. It has also been observed that the portions of the catheter near each end of the balloon and in contact with mandrel 110 are deflected radially inwardly and heat-set in that condition, and that this creates valley-like "ramps" which help the balloon refold when it is deflated. FIG. 18 shows such a ramp 112 in inflation lumen 30 near the proximal end of balloon 50. A similar ramp may be formed near the distal end of balloon 50. Each such ramp is an axial extension of a fold in balloon 50 into the wall of the lumen 40 and/or 60 which includes that ramp. (Ramps like those described above may alternatively be formed earlier in the manufacture of the catheter. For example, the tooling or processing which joins the balloon to proximal and distal lumens 30 and 60 may form and heat-set ramps like 112 into lumens 30 and 60 and the adjacent portions of balloon 50. In that event, the above-described processing using mandrel 110 may do no more than reinforce the already formed ramps.)

After the balloon has been heat set as described above, the catheter may be further processed (e.g., to add stent 70, to add an elastic sleeve structure 100 if such a structure is desired, and to withdraw mandrel 110). These additional processing steps may be performed in any suitable order. After mandrel 110 has been withdrawn, the above-described heat set of the catheter keeps open the above-described clearance through the balloon for the guide wire.

It will be understood that the foregoing is only illustrative of the principles of this invention and that various modifications can be made by those skilled in the art without departing from the scope and spirit of the invention. For example, it may not be necessary to provide a guide wire lumen proximal of balloon 50, and in that case lumen 40 may be omitted.

The invention claimed is:

1. A balloon catheter system comprising:
   an initially deflated inflatable balloon;
   a guidewire: and
   a stent structure disposed on said balloon and forming an annulus around said balloon, said guidewire padding axially along said balloon inside the annulus formed by said stent structure but outside said balloon.

2. The catheter system defined in claim 1 wherein said stent structure is substantially the sole structure at the location of said balloon for positively maintaining said balloon adjacent to said guide wire.

3. The catheter system defined in claim 2 wherein, in its initially deflated condition, said balloon is folded laterally on itself in a plurality of folds between which said guide wire can pass, and wherein said stent structure maintains said folds in said balloon until said balloon is inflated.

4. The catheter system defined in claim 1 wherein, in its initially deflated condition, said balloon is folded laterally on itself in a plurality of folds, between which said guide wire can pass, and wherein said stent structure maintains said folds in said balloon until said balloon is inflated.

5. The catheter system defined in claim 4 wherein said balloon is folded so that an axial clearance is left between folds of the balloon, through which clearance said guide wire can pass axially along said balloon and wherein a portion of said balloon is intermediate said guide wire and said stent structure.

6. The catheter system defined in claim 5 wherein said clearance is produced by folding said balloon around a mandrel at the desired location of said clearance, heat setting the folded balloon, and withdrawing said mandrel to leave said clearance.

7. The catheter system defined in claim 6 wherein said balloon has axially opposite proximal and distal ends from which proximal and distal lumens respectively extend, and wherein said mandrel presses radially inwardly on portions of said lumens adjacent to said proximal and distal ends so that heat setting the folded balloon also heat sets the portions of said lumens that are pressed radially inwardly to help promote refolding of the balloon after use of the catheter system to implant the stent structure.

8. The catheter system defined in claim 5 wherein said balloon has axially opposite proximal and distal ends, and wherein said catheter system further comprises:
   a distal guide wire lumen extending distally of said distal end of said balloon for allowing a guide wire portion which is distal of said balloon to pass through said distal guide wire lumen, said distal guide wire lumen having a proximal extension which extends into a distal portion of said clearance.

9. The catheter system defined in claim 8 wherein said extension of said distal guide wire lumen has a proximal end which is distal of a distal end of said stent structure.

10. The catheter system defined in claim 5 wherein said balloon has axially opposite proximal and distal ends, and wherein said catheter system further comprises:

a proximal guide wire lumen extending proximally of said proximal end of said balloon for allowing a guide wire portion which is proximal of said balloon to pass through said proximal guide wire lumen, said proximal guide wire lumen having a distal extension which extends into a proximal portion of said clearance.

11. The catheter system defined in claim 10 wherein said extension of said proximal guide wire lumen has a distal end which is proximal of a proximal end of said stent structure.

12. The catheter system defined in claim 1 wherein said stent structure is circumferentially expandable in response to inflation of said balloon.

13. The catheter system defined in claim 1 wherein said balloon has axially opposite proximal and distal ends, and wherein said catheter system further comprises:

a distal guide wire lumen extending distally of said distal end of said balloon for allowing a guide wire portion which is distal of said balloon to pass through said distal guide wire lumen.

14. The catheter system defined in claim 1 wherein said balloon has axially opposite proximal and distal ends, and wherein said catheter system further comprises:

a proximal guide wire lumen extending proximally of said proximal end of said balloon for allowing a guide wire portion which is proximal of said balloon to pass through said proximal guide wire lumen.

15. The catheter system defined in claim 1 wherein said balloon has axially opposite proximal and distal ends, and wherein said catheter system further comprises:

an inflation lumen extending proximally from the proximal end of said balloon, said inflation lumen being in fluid communication with the interior of said balloon for supplying pressurized inflation fluid to said balloon for inflating said balloon.

16. The catheter system defined in claim 15 further comprising:

a proximal guide wire lumen extending along said inflation lumen for allowing a guide wire portion which is proximal of said balloon to pass through said proximal guide wire lumen.

17. The catheter system defined in claim 16 wherein said proximal guide wire lumen extends along only a portion of said inflation lumen that is relatively close to said balloon.

18. The catheter system defined in claim 1 further comprising:

a radio-opaque marker adjacent to said balloon.

19. The catheter system defined in claim 1 wherein said balloon has axially opposite proximal and distal ends, and wherein said catheter system further comprises:

a pusher wire attached to the catheter at a location which is adjacent the distal end of said balloon and extending proximally from said location and from the proximal end of said balloon.

20. The catheter system defined in claim 19 wherein said pusher wire is made of nitinol.

21. The catheter system defined in claim 19 wherein said pusher wire has a distal portion which is distal of the distal end of said balloon, said distal portion being formed into an axially extending coil through which a portion of the guide wire distal of said balloon can pass.

22. The catheter system defined in claim 19 wherein said pusher wire passes axially through the interior of said balloon, and wherein said catheter system further comprises:

a radio-opaque marker on said pusher wire.

23. The catheter system defined in claim 22 wherein said radio-opaque marker is axially adjacent to an axial end of said stent structure.

24. The catheter system defined in claim 23 further comprising:

a second radio-opaque marker on said pusher wire axially adjacent to a second axial end of said stent structure.

25. The catheter system defined in claim 1 wherein said balloon and said stent structure are formed to provide a clearance through which said guide wire can pass axially along said balloon inside the annulus formed by said stent structure but outside said balloon and wherein a portion of said balloon is intermediate said guide wire and said stent structure.

26. The catheter system defined in claim 25 wherein said clearance is produced by heat setting said balloon in contact with a mandrel disposed at the desired location of said clearance, and then withdrawing said mandrel to leave said clearance.

27. The catheter system defined in claim 1 wherein said balloon has axially opposite proximal and distal ends from which proximal and distal lumens respectively extend, wherein in its initially deflated condition said balloon is folded laterally on itself in a plurality of folds, and wherein at least one of said lumens has an axially extending valley-like ramp in its wall which forms an axial continuation of a fold in said balloon.

28. A balloon catheter system comprising:

an initially deflated inflatable balloon;

a guidewire;

an annular elastic sleeve structure disposed around said balloon for resiliently circumferentially compressing said balloon; and a stent structure disposed on said balloon and forming an annulus around said balloon, said guidewire passing axially along said balloon inside the annulus formed by said stent structure but outside said balloon.

29. The catheter system defined in claim 28 wherein said guide wire passes axially along said balloon outside of said sleeve structure, and wherein said stent structure is substantially the sole structure at the location of said balloon for positively maintaining said balloon adjacent to said guide wire.

30. The catheter system defined in claim 28 wherein said guide wire passes axially along said balloon inside said sleeve structure.

31. The catheter system defined in claim 30 wherein, in its initially deflated condition, said balloon is folded laterally on itself in a plurality of folds, between which said guide wire can pass, and wherein said sleeve structure and said stent structure maintain said folds in said balloon until said balloon is inflated.

32. The catheter system defined in claim 28 wherein, in its initially deflated condition, said balloon is folded laterally on itself in a plurality of folds, between which said guide wire can pass, and wherein said sleeve structure and said stent structure maintain said folds in said balloon until said balloon is inflated.

33. The catheter system defined in claim 28 wherein said sleeve structure and said stent structure are circumferentially expandable in response to inflation of said balloon.

34. The catheter system defined in claim 28 wherein said sleeve structure is axially spaced from said stent structure.

35. The catheter system defined in claim 34 wherein said sleeve structure comprises:

a proximal portion which is proximal of a proximal end of said stent structure; and a distal portion which is distal of a distal end of said stent structure.

36. The catheter system defined in claim 28 wherein said stent structure axially overlaps said sleeve structure.

37. The catheter system defined in claim 36 wherein said stent structure surrounds at least a portion of said sleeve structure.

38. The catheter system defined in claim 28 wherein said balloon has axially opposite proximal and distal ends from which proximal and distal lumens respectively extend, wherein at least one of said lumens has a port in its wall adjacent said balloon for emergence of said guide wire from the at least one lumen in a direction toward said balloon, and wherein said sleeve extends axially from said balloon to a point which is axially beyond said port.

39. A balloon catheter system and guide wire system comprising:

an initially deflated inflatable balloon;

a guide wire passing axially along said balloon without traversing the interior of said balloon; and an annular stent structure disposed around said balloon and said guide wire at the location of said balloon for keeping said balloon adjacent to said guide wire at the location of the balloon.

40. The system defined in claim 39 wherein said balloon and said stent structure are movable together axially relative to said guide wire.

41. The system defined in claim 39 wherein said guide wire passes between said balloon and said stent structure.

42. The system defined in claim 39 wherein, in its initially deflated condition, said balloon is folded laterally into a plurality of folds, and wherein said guide wire passes along said balloon between said folds.

43. The system defined in claim 42 wherein said stent structure maintains said folds in said balloon until said balloon is inflated.

44. The system defined in claim 42 wherein said balloon is folded so that an axial clearance is left between folds of the balloon, through which clearance said guide wire can pass axially along said balloon and wherein a portion of said balloon is intermediate said guide wire and said stent structure.

45. The system defined in claim 44 wherein said clearance is produced by folding said balloon around a mandrel at the desired location of said clearance, heat setting the folded balloon, and withdrawing said mandrel to leave said clearance.

46. The system defined in claim 45 wherein said balloon has axially opposite proximal and distal ends from which proximal and distal lumens respectively extend, and wherein said mandrel presses radially inwardly on portions of said lumens adjacent said proximal and distal ends so that heat setting the folded balloon also heat sets the portions of said lumens that are pressed radially inwardly to help promote refolding of the balloon after use of the catheter to implant the stent structure.

47. The system defined in claim 44 wherein said balloon has axially opposite proximal and distal ends, and wherein the catheter further comprises:

a distal guide wire lumen extending distally of said distal end of said balloon for allowing a guide wire portion which is distal of said balloon to pass through said distal guide wire lumen, said distal guide wire lumen having a proximal extension which extends into a distal portion of said clearance.

48. The system defined in claim 47 wherein said extension of said distal guide wire lumen has a proximal end which is distal of a distal end of said stent structure.

49. The system defined in claim 44 wherein said balloon has axially opposite proximal and distal ends, and wherein the catheter further comprises:

a proximal guide wire lumen extending proximally of said proximal end of said balloon for allowing a guide wire portion which is proximal of said balloon to pass through said proximal guide wire lumen, said proximal guide wire lumen having a distal extension which extends into a proximal portion of said clearance.

50. The system defined in claim 49 wherein said extension of said proximal guide wire lumen has a distal end which is proximal of a proximal end of said stent structure.

51. The system defined in claim 39 wherein said stent structure is circumferentially expandable in response to inflation of said balloon.

52. The system defined in claim 39 wherein said balloon has axially opposite proximal and distal ends, and wherein the catheter further comprises:

a distal guide wire lumen extending distally of said distal end of said balloon for allowing a guide wire portion which is distal of said balloon to pass through said distal guide wire lumen.

53. The system defined in claim 39 wherein said balloon has axially opposite proximal and distal ends, and wherein the catheter further comprises:

a proximal guide wire lumen extending proximally of said proximal end of said balloon for allowing a guide wire portion which is proximal of said balloon to pass through said proximal guide wire lumen.

54. The system defined in claim 39 wherein said balloon has axially opposite proximal and distal ends, and wherein the catheter further comprises:

an inflation lumen extending proximally from the proximal end of said balloon, said inflation lumen being in fluid communication with the interior of said balloon for supplying pressurized inflation fluid to said balloon for inflating said balloon.

55. The system defined in claim 54 further comprising:

a proximal guide wire lumen extending along said inflation lumen for allowing a guide wire portion which is proximal of said balloon to pass through said proximal guide wire lumen.

56. The system defined in claim 55 wherein said proximal guide wire lumen extends along only a portion of said inflation lumen that is relatively close to said balloon.

57. The system defined in claim 39 further comprising:

a radio-opaque marker adjacent to said balloon.

58. The system defined in claim 39 wherein said balloon has axially opposite proximal and distal ends, and wherein the catheter further comprises:

a pusher wire attached to said catheter at a location which is adjacent the distal end of said balloon and extending proximally from said location and from the proximal end of said balloon.

59. The system defined in claim 58 wherein said pusher wire is made of nitinol.

60. The system defined in claim 58 wherein said pusher wire has a distal portion which is distal of the distal end of said balloon, said distal portion being formed into an axially extending coil through which a portion of the guide wire distal of said balloon can pass.

61. The system defined in claim 58 wherein said pusher wire passes axially through the interior of said balloon, and wherein said catheter further comprises:

a radio-opaque marker on said pusher wire.

62. The system defined in claim 61 wherein said radio-opaque marker is axially adjacent an axial end of said stent structure.

63. The system defined in claim 62 further comprising:
   a second radio-opaque marker on said pusher wire axially adjacent a second axial end of said stent structure.

64. The system defined in claim 39 wherein said balloon and said stent structure are formed to provide a clearance through which said guide wire can pass axially along said balloon inside the annulus formed by said stent structure but outside said balloon and wherein a portion of said balloon is intermediate said guide wire and said stent structure.

65. The system defined in claim 64 wherein said clearance is produced by heat setting said balloon in contact with a mandrel disposed at the desired location of said clearance, and then withdrawing said mandrel to leave said clearance.

66. The system defined in claim 39 wherein said balloon has axially opposite proximal and distal ends from which proximal and distal lumens respectively extend, wherein in its initially deflated condition said balloon is folded laterally on itself in a plurality of folds, and wherein at least one of said lumens has an axially extending valley-like ramp in its wall which forms an axial continuation of a fold in said balloon.

67. The system defined in claim 39 further comprising:
   an annular elastic sleeve structure around said balloon for resiliently circumferentially compressing said balloon.

68. The system defined in claim 67 wherein said sleeve structure is axially spaced from said stent structure.

69. The system defined in claim 68 wherein said sleeve structure comprises:
   a proximal portion which is proximal of a proximal end of said stent structure; and
   a distal portion which is distal of a distal end of said stent structure.

70. The system defined in claim 67 wherein said stent structure surrounds said sleeve structure.

71. The system defined in claim 70 wherein said guide wire passes between said sleeve structure and said stent structure.

72. The system defined in claim 67 wherein said balloon has axially opposite proximal and distal ends from which proximal and distal lumens respectively extend, wherein at least one of said lumens has a port in its wall adjacent said balloon for emergence of said guide wire from said lumen in a direction toward said balloon, and wherein said sleeve extends axially from said balloon to a point which is axially beyond said port.

73. A stent delivery catheter system comprising:
   an annular stent structure;
   a balloon having an interior, proximal and distal ends, and an initially deflated configuration wherein the balloon is laterally folded in on itself in a plurality of folds, the annular stent structure retaining the balloon in the initially deflated configuration;
   a guidewire;
   a proximal lumen communicating with the interior of the balloon; and
   a guidewire lumen having a distal end disposed proximally of the proximal end of the balloon member, the guidewire disposed for translation through the guidewire lumen so as to exit the distal end of the guidewire lumen and pass between the plurality of folds of the balloon.

74. The delivery catheter system as defined in claim 73 further comprising a distal guide wire lumen disposed from the distal end of the balloon.

75. The delivery catheter system as defined in claim 73 wherein the balloon maintains the initially deflated configuration until said balloon is inflated.

76. A balloon catheter system comprising:
   a balloon having an interior, proximal and distal ends, and an initially deflated configuration wherein the balloon is laterally folded in on itself in a plurality of folds;
   an elastic annular member disposed around the balloon to retain the balloon in the initially deflated configuration;
   a proximal lumen communicating with the interior of the balloon;
   a guidewire; and
   a guidewire lumen having a distal end disposed proximally of the proximal end of the balloon, the guidewire disposed for translation through the guidewire lumen so as to exit the distal end of the guidewire lumen and pass between the plurality of folds of the balloon.

77. The balloon catheter system as defined in claim 76 further comprising a distal guide wire lumen disposed from the distal end of the balloon.

78. The balloon catheter system as defined in claim 76 wherein the balloon maintains the initially deflated configuration until said balloon is inflated.

* * * * *

UNITED STATES PATENT AND TRADEMARK OFFICE
CERTIFICATE OF CORRECTION

PATENT NO. : 6,071,285
DATED : June 6, 2000
INVENTOR(S) : Lashinski et al.

It is certified that error appears in the above-identified patent and that said Letters Patent is hereby corrected as shown below:

In the abstract, last line, please delete "inside" and insert --either inside or outside-- therefor.

In Column 10
Line 19, please delete "padding" and insert --passing-- therefor.

Signed and Sealed this

Twelfth Day of June, 2001

*Attest:*

*Attesting Officer*

NICHOLAS P. GODICI
*Acting Director of the United States Patent and Trademark Office*